United States Patent
Chen et al.

(10) Patent No.: US 10,610,181 B2
(45) Date of Patent: Apr. 7, 2020

(54) ROBUST CALCIFICATION TRACKING IN FLUOROSCOPIC IMAGING

(71) Applicant: Siemens Healthcare GmbH, Erlangen (DE)

(72) Inventors: Terrence Chen, Princeton, NJ (US); Sarfaraz Hussein, Orlando, FL (US); Matthias John, Nürnberg (DE); Vivek Kumar Singh, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 22 days.

(21) Appl. No.: 15/548,581

(22) PCT Filed: Feb. 12, 2016

(86) PCT No.: PCT/EP2016/052988
§ 371 (c)(1),
(2) Date: Aug. 3, 2017

(87) PCT Pub. No.: WO2016/134980
PCT Pub. Date: Sep. 1, 2016

(65) Prior Publication Data
US 2018/0008222 A1    Jan. 11, 2018

Related U.S. Application Data

(60) Provisional application No. 62/121,538, filed on Feb. 27, 2015, provisional application No. 62/121,543, filed on Feb. 27, 2015.

(51) Int. Cl.
*A61B 6/00*  (2006.01)
*A61B 6/12*  (2006.01)
(Continued)

(52) U.S. Cl.
CPC ............ *A61B 6/504* (2013.01); *A61B 6/12* (2013.01); *A61B 6/487* (2013.01); *A61B 6/5211* (2013.01);
(Continued)

(58) Field of Classification Search
CPC .......... A61B 6/12; A61B 6/487; A61B 6/504; A61B 6/5211; G06F 19/00; G06T 7/246;
(Continued)

(56) References Cited

U.S. PATENT DOCUMENTS 3,938,506 A * 2/1976 Birnbaum ............ A61B 5/0215
600/486
5,768,405 A * 6/1998 Makram-Ebeid ..... G06T 7/0012
382/128
(Continued)

FOREIGN PATENT DOCUMENTS

WO    2014124447    8/2014

OTHER PUBLICATIONS

International Search Report for Corresponding International Patent Application No. PCT/EP2016/052988, dated Apr. 29, 2016.
(Continued)

*Primary Examiner* — Mekonen T Bekele

(57) ABSTRACT

Robust calcification tracking is provided in fluoroscopic imagery. A patient with an inserted catheter is scanned over time. A processor detects the catheter in the patient from the scanned image data. The processor tracks the movement of the catheter. The processor also detects a structure represented in the data. The structure is detected as a function of movement with a catheter. The processor tracks the movement of the structure using sampling based on a previous location of the structure in the patient. The processor may output an image of the structure.

20 Claims, 4 Drawing Sheets

(51) Int. Cl.
*G06T 7/246* (2017.01)
*G06T 7/73* (2017.01)

(52) U.S. Cl.
CPC .............. *G06T 7/246* (2017.01); *G06T 7/73* (2017.01); *G06T 2207/10121* (2013.01); *G06T 2207/20081* (2013.01); *G06T 2207/30101* (2013.01)

(58) Field of Classification Search
CPC ............ G06T 7/73; G06T 2207/10121; G06T 2207/20081; G06T 2207/30101
See application file for complete search history.

(56) References Cited

U.S. PATENT DOCUMENTS

| | | | | | |
|---|---|---|---|---|---|
| 5,971,927 | A | * | 10/1999 | Mine | A61B 8/06 600/455 |
| 7,317,825 | B2 | * | 1/2008 | Yang | G06T 15/08 345/420 |
| 8,391,957 | B2 | * | 3/2013 | Carlson | A61M 25/0662 600/429 |
| 2006/0147106 | A1 | * | 7/2006 | Yang | G06T 15/08 382/154 |
| 2008/0020362 | A1 | * | 1/2008 | Cotin | G16H 50/50 434/267 |
| 2008/0177138 | A1 | * | 7/2008 | Courtney | A61B 5/0062 600/109 |
| 2008/0211812 | A1 | * | 9/2008 | Barbu | G06K 9/00201 345/424 |
| 2009/0154785 | A1 | * | 6/2009 | Lynch | G06T 7/33 382/131 |
| 2009/0264768 | A1 | * | 10/2009 | Courtney | A61B 5/0062 600/463 |
| 2011/0106232 | A1 | * | 5/2011 | Broome | A61B 5/053 607/119 |
| 2011/0164035 | A1 | * | 7/2011 | Liao | G06T 7/246 345/419 |
| 2011/1064035 | | | 7/2011 | Liao et al. | |
| 2012/0123250 | A1 | * | 5/2012 | Pang | A61B 6/12 600/424 |
| 2012/0238866 | A1 | * | 9/2012 | Wang | A61B 6/12 600/424 |
| 2013/0011030 | A1 | * | 1/2013 | Tzoumas | G06K 9/6282 382/128 |
| 2013/0072773 | A1 | * | 3/2013 | Wu | A61B 6/12 600/373 |
| 2013/0279825 | A1 | * | 10/2013 | Liao | G06T 11/60 382/284 |
| 2014/0176685 | A1 | * | 6/2014 | Oikawa | G06T 15/08 348/51 |
| 2015/0171792 | A1 | * | 6/2015 | Kim | H02N 2/008 310/317 |
| 2017/0135590 | A1 | * | 5/2017 | Itagaki | A61B 5/055 |

OTHER PUBLICATIONS

Karar, et al., "A simple and accurate method for computer-aided transapical aortic valve replacement" Computerized Medical Imaging and Graphics, Sep. 1, 2014 (Sep. 1, 2014).

* cited by examiner

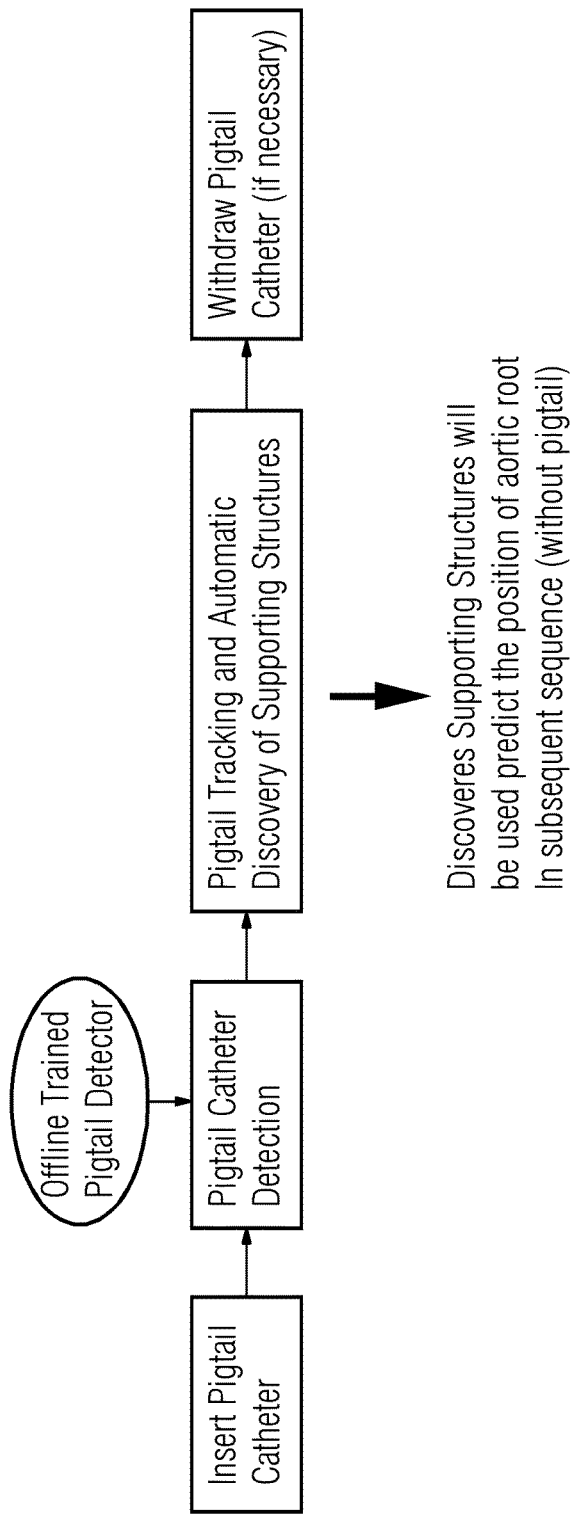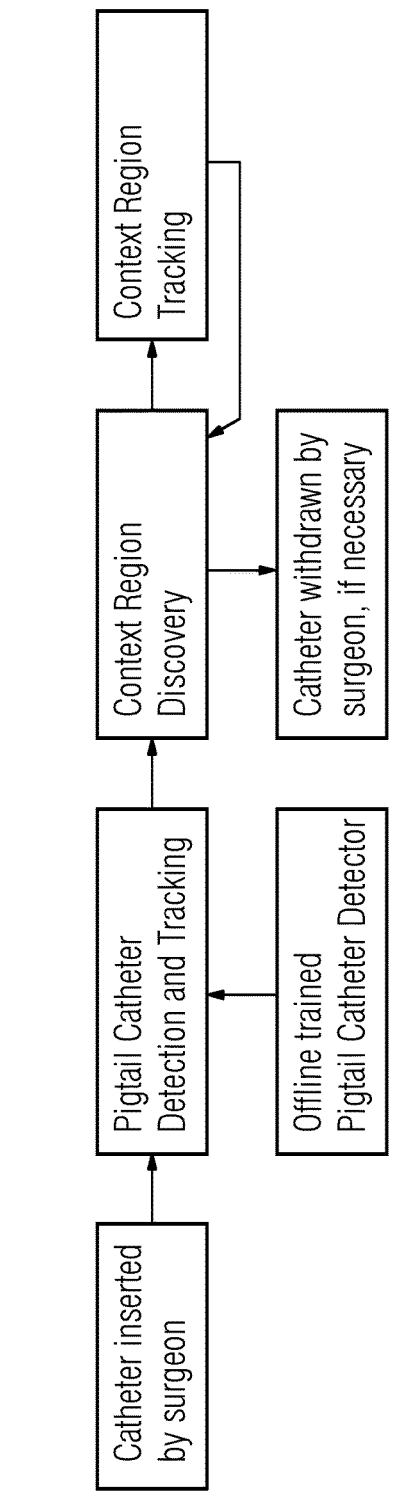

50     52     54

ROBUST CALCIFICATION TRACKING IN FLUOROSCOPIC IMAGING

BACKGROUND

The present embodiments relate to tracking anatomical structures in images of a patient. During surgery, surgeons often use fluoroscopy as a visual aid to perform the procedure. However, the position of anatomical structures may not be clearly visible in fluoroscopic images and may be difficult to track visually due to cardiac, as well as respiratory, movement. Existing methods require an operator to carefully mark a predefined set of landmarks for the tracking of an anatomical structure. Often these markers must be updated during the procedure. Although detection based trackers that employ offline trained detectors perform well for tracking known structures, their performance to track certain anatomical structures without a known shape in advance is still limited. One method currently in use to track the position and orientation of, for example, an aortic root is by injecting an iodinated contrast agent (angiography) into the patient. However, such contrast agents are harmful for the patient and their use should be minimized. Due to this, surgeons often must carefully weigh the benefits of the use of contrast agents for a successful procedure compared to the patient's safety due to the contrast agent's side effects to the patients. Alternatively, semi-supervised trackers that learn an objects appearance perform well but are very sensitive to initialization.

BRIEF SUMMARY

By way of introduction, the preferred embodiments described below include methods, systems, instructions, and non-transitory computer readable media for tracking objects in medical imagery, such as fluoroscopic imagery. A catheter is inserted into a patient. The structure of the catheter is known in advance. This allows for the detection and tracking of the catheter. By knowing how the catheter looks inside the patient, the movement of the catheter is tracked. Using a catheter also negates the need to do manual initialization for the tracking algorithm. The system knows what to look for because the catheter imaged characteristics are known in advance. For example, during a Transcatheter Aortic Valve Implantation (TAVI) procedure, the catheter is located near the aortic root. If the surgeon needs to track anatomical structures, such as calcium deposits, the system tracks the movement of the catheter. The catheter moves in synchronization with the aortic root. The system detects any other anatomical structures which are moving in sync with the catheter. These structures are, for example, calcium deposits. As the procedure proceeds, the system tracks the detected structure using a sampling strategy. The sampling strategy, such as using a discrete structure forest, is applied to track the detected structure.

In a first aspect, a method is provided for tracking and detecting a structure in a patient. A patient with an inserted catheter is scanned over time. A processor detects the catheter in the patient from the scanned image data. The processor tracks the movement of the catheter. The processor also detects a structure represented in the data from the scanning that is detected as a function of movement with a catheter. The processor tracks the movement of the structure using sampling based on a previous location of the structure in the patient. The processor may output an image of the structure.

In a second aspect, a system is provided for object detection over time in a patient with an inserted catheter. The system includes a scanner and a processor. The scanner is configured to image the patient with the inserted catheter over time. The processor is configured to detect and track the catheter as represented in the scanned data from the imaging. The processor is further configured to detect and track an object represented in the data from the imaging where the object is detected as a function of movement with the catheter. The object is tracked using sampling based on a previous location of the object. The processor is configured to output an image of the object.

In a third aspect, a non-transitory computer readable storage medium having stored therein data representing instructions executable by a programmed processor for facilitating detection of an object in a patient. The instructions include scanning a patient over time having an inserted pig tail catheter. The processor, according to the instructions, detects the pig tail catheter. The movement of the pig tail catheter is tracked. The processor, according to the instructions, detects a structure represented in the data from the scanning. The structure is detected as a function of movement with the catheter. The processor tracks the structure represented in the data from the scanning. The tracking uses sampling based on a previous location of the structure. The processor may output an image of the structure.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 is a flowchart of another embodiment for tracking anatomical structures in medical images;

FIG. 4 is a flowchart of an alternative embodiment for tracking anatomical structures in medical images;

DETAILED DESCRIPTION OF THE DRAWINGS AND PRESENTLY PREFERRED EMBODIMENTS

Manual detection of objects in a patient may be tedious and difficult due to the high variability in object shape and the movement occurring from the patient's organs. For automatic detection, the initialization process may be complicated by determining where to place markers for detection algorithms to begin their detection and tracking of the objects. These problems may be solved by detecting and tracking a catheter that has been inserted into a patient. The catheter has a known shape and thus may act as the initialization marker for the detection and tracking algorithm to locate anatomy.

Figure 1:
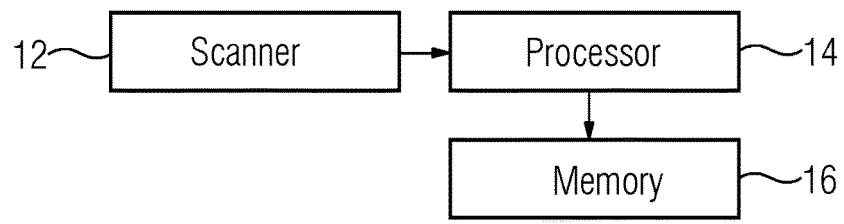
FIG. 1 illustrates an example system for tracking structures in medical images.
Figure 2:
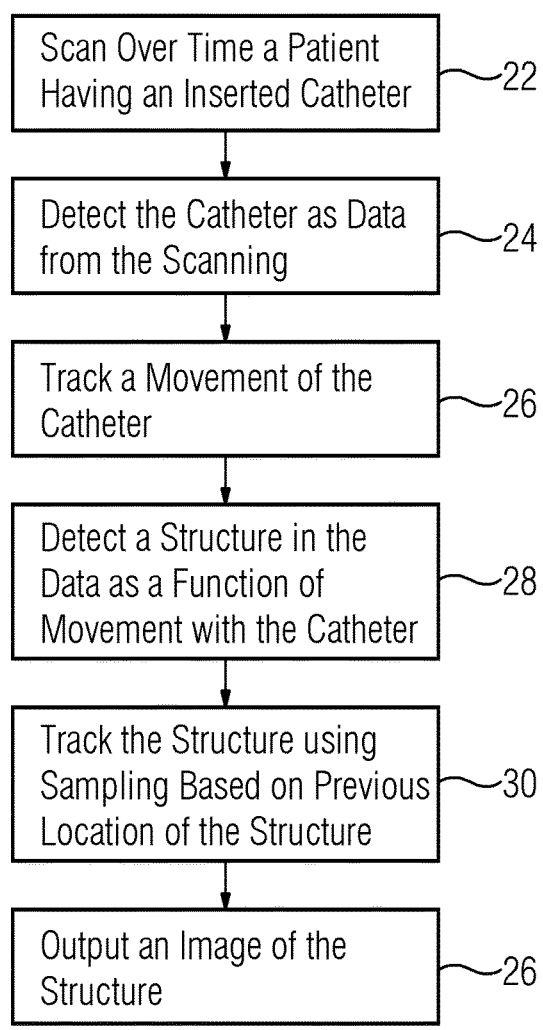
FIG. 2 is one embodiment of a flow chart diagram for tracking anatomical structures in medical images.

FIG. 2 is a flow chart diagram of one embodiment of a method for detecting objects in a patient. The method is implemented by the system of FIG. 1, a scanner, a processor, a memory, or another system. For example, a fluoroscopic scanner images a patient and the processor and memory of the scanner utilize the images to aid in the detection of objects within a patient.

The method includes detecting and tracking a structure in a patient. The structure may be an anatomical structure, or the structure may be a foreign object inserted inside the patient, such as a stent. The detecting and tracking includes analyzing images from medical scanners, such as fluoroscopic scanners. For example, during a procedure, such as a TAVI procedure, a patient with an inserted catheter may be imaged by a fluoroscopic scanner. From the imaging data, additional objects that are moving in unison with the inserted catheter are detected and tracked. Once detected the objects may be tracked throughout the procedure. Other types of imaging, such as computed tomographic, ultrasound, or magnetic resonance may be used. Other inserted devices than a catheter may be used, such as a fiducial or stent.

The acts are performed in the order shown (e.g., top to bottom) or other orders. Additional, different, or fewer acts may be provided. For example, the method is performed without outputting the image in act 32. As another example, acts 24 and 26 are alternatives or not provided at all (e.g., detect in act 24 for each time or track over time in act 26 without further detection).

In act 22, a patient having an inserted catheter is scanned. In alternative embodiments the patient has an inserted stent. The stent may be used in the same manner as the catheter for detection and/or tracking purposes. The inserted catheter may be a pigtail catheter. In some embodiments a stent and catheter may both be inserted and work in conjunction to aid in the detecting and tracking process.

The scanning may be done by a fluoroscopic scanner, or another type of scanner used for medical imaging. The scanning may also aid in identifying the location and movement of the patients organs, such as, for example, the heart. The scanner may be affixed to the system of FIG. 1, such as the scanner 12. In other embodiments, the scan data may be produced from the memory 16 of FIG. 1. The scanning may be done prior to the method depicted in FIG. 2. In some embodiments, the scanning is performed continuously or periodically over time for the operation of the method depicted in FIG. 2. The scanner images the patient having the inserted catheter.

In some embodiments the catheter is inserted at the aortic root of the patient. The catheter may have a hook which allows the catheter to stay affixed to the aortic root of the patient. In some embodiments, the catheter is kept inserted in the patient until an artificial valve is about to be inserted. The inserted catheter may be removed during the procedure. In other embodiments the catheter remains inserted during the entire procedure.

In act 24, the catheter is detected in data produced by the scanning of the patient with the scanner. The detecting may be done by the processor 14 of the system depicted in FIG. 1. In some embodiments the processor detects the catheter using instructions stored in the memory 16 of the system depicted in FIG. 1. Example methods for detecting the catheter are described below with respect to FIGS. 3 and 4. In some embodiments, the projected position of the catheter may be included as an input for the detecting of the catheter. The shape of the catheter is known in advance and the detection process may be enhanced by offline machine detection training to speed up the process of detecting the catheter once inserted in the patient. The offline trained catheter detector may store the results of the training in the memory 16 of the system depicted in FIG. 1, so the processor 14 may access the results while attempting to detect the catheter in data from a scan of a given patient. The data may include a plurality of fluoroscopic images. In some embodiments the plurality of fluoroscopic images corresponds to a live stream of images of the patient. The image may be formatted as display values (e.g., RGB or grayscale) or may be intensity values prior to display mapping and display.

The detection is performed for a given image, such as a first image in a sequence of images. The detection relies on spatial indication of the catheter. For other times or images in the sequence, the detection is repeated. Alternatively, tracking is used. The identified catheter is tracked rather than re-applying the detection. In other embodiments, the detection is repeated to update the tracking (e.g., repeat detection for each heart cycle) or detection is provided instead of tracking.

In act 26, a movement of the catheter may be tracked. The processor tracks the catheter. The tracking may include using stored images of the catheter in the memory to supplement the tracking. The catheter is detected through a sequence of images by redetecting the catheter in each image. As the patient is imaged, the movement of the inserted catheter is tracked based on an expected shape, such as detecting using a template matching or a machine-trained classifier. In other embodiments, the catheter is detected in one image or frame of data. The catheter is then tracked by determining a translation, rotation, and/or scale associated with a greatest similarity. For example, the intensities representing the catheter from one image are translated, rotated, and/or scaled and compared using sum of absolute differences or other correlation to a subsequent image. The translation, rotation, and/or scale with the greatest similarity indicates the catheter position in the subsequent image.

The disclosed embodiments do away with the need to manually indicate in the data markers for potential object detecting and tracking by tracking the movement of the catheter. This method is particularly useful given the rapid rate of movement caused by respiration and cardiac movement in the patient compared to the frame rate at which the patient is imaged.

In act 28, the processor may detect an object, or structure, represented in the data from the scanning. The object may be a support region. The object may be an anatomical structure. In some cases, the anatomical structure has no known features or structure in advance of the scanning. In other cases, the anatomical structure is known in advance and a template of what the structure may look like in the data may be used to help with detecting the structure. In some embodiments the object detected may be an inserted object separate from the catheter, such as a small tube, or stent.

The object may be detected as a function of movement with the catheter. A support region is defined as having a linear motion correlation with a known anatomical structure, such as an aortic root. Image regions may be easier to detect and track because the image regions allow use of appropriate non-local appearance models that are more robust to image noise, optical-flow failures. The catheter, having been inserted near a known anatomical structure, will move in sync with the movement of the known anatomical structure, such as for example a heart, aortic root, or lung. As such, any other structures moving in sync with the inserted catheter are necessarily moving in sync with the aortic root, heart, or lung. The structures may be anatomical structures, such as calcium deposits or tumors, as an example, with no known shape prior to a procedure on the patient. Tracked tumors may be tumor regions in lung fluoroscopic images.

In some embodiments, support regions are created by the use of local support points. Standard feature sampling techniques, such as image segmentation, image registration, image-based physiological modeling, or statistical analysis, are used to discover local support points in the initial frames or images that make up the data from the scanning. The local support points are assumed to lie in the same local motion space. The processor may use an autoregressive model to model point-to-point linear motion correlation between the inserted catheter and a potential object in a given time period. The correlation may be represented as a correlation score. A clustering algorithm may be used to group the point trajectories based on spatial and motion cues in the potential support regions. A metric is used that captures the similarity in spatial location and motion. In general, if two trajectories are close to each other and move similarly then the trajectories likely belong to the same region. A trajectory $T_a = \{p_a^i = (x_a^i, y_a^i): i \in A\}$ is represented as a sequence of points $p_a^i$ that spans frames in the set A, for example the data scanned from the patient. At any moment, in a current frame, the distance between trajectory $T_a$ and $T_b$ is the spatial distance $d_S^i(T_a, T_b)$ and motion distances $d_M^i(T_a, T_b)$ where $d(T_a, T_b)$:

$$d_M^i(T_a, T_b) = \frac{\left(u_a^{i-\Delta:i} - u_b^{i-\Delta:i}\right)^2}{\left(\delta_{Mu}^i\right)^2} + \frac{\left(v_a^{i-\Delta:i} - v_b^{i-\Delta:i}\right)^2}{\left(\delta_{Mv}^i\right)^2} \quad \text{(Eq. 1)}$$

and $$d_S^i(T_a, T_b) = \|p_a^i - p_b^i\| / \delta_S^2 \quad \text{(Eq. 2)}$$

$\delta_{Mu}^i$ and $\delta_{Mv}^i$ are standard deviations of motion in each axis that are used to normalize the weights of motion in both distances. $\delta_S$ is a normalizing parameter of spatial distance that can be tuned to balance motion and spatial distance. $\Delta$ is a motion smoothness parameter. Distance over nearby t frames in the fluoroscopic data is computed by:

$$d_M^{1:t}(T_a, T_b) = \text{median}_{\{i-\Delta,i\} \in x} d_M^i(T_a, T_b) \quad \text{(Eq. 3)}$$

$$d_S^{1:t}(T_a, T_b) = \text{median}_{i \in x} d_S^i(T_a, T_b) \quad \text{(Eq. 4)}$$

Where $X = \{x: x < t, x \in A \cap B\}$ is the set of overlapping frames to time t. The median of frame-wise distance is taken, since the median is more robust to trajectory noise than maximum and average distance. Affinity matrix of all trajectories in current frame is constructed from distance by:

$$W^r = \text{Exp}(-(D_M^t + )D_S^t) \quad \text{(Eq. 5)}$$

The number of clusters is automatically determining by analyzing low dimensional embedding of point trajectory space. This automatic motion compensation scheme has a strong motion correlation with an aortic root, for example, as well as improves the performance of motion estimation by calcium tracking. The technique recited above may obviate the need for contrast agents to detect human anatomy, such as a patient's aortic root.

By using the trajectories of the local support regions, the system is able to detect the structure by the structure's associated movement with the inserted catheter. The trajectories are used to detect the structure as the structure moves in synchronization with the catheter. This detection is of the structure in a given frame or image, but is based on the trajectories over a sequence. In some embodiments, only some structures are selected for tracking based on the correlation score. The structures with the highest correlation scores may be selected for the tracking.

In act 30, the structure, as represented in the data, may be tracked. The processor 14 of the system depicted in FIG. 1 may track the structure. The structure may be tracked by sampling locations in an image based on a previous location of the structure, and using those locations to predict the structure's location in future images. In some embodiments, the imaging of the patient produces a plurality of fluoroscopic images. The structure may be tracked by tracking features of the structure. In some embodiments the structure may be tracked by using discrete structure forests. Tracking the structure may include tracking the density of the structure, tracking the contrast between the structure and the surrounding areas in the data, random sampling of points in the structure and outside the structure or a combination thereof. In some embodiments, the tracking includes constructing a bounding box around the detected structure. The bounding box may be automatically constructed by the processor 12 of the system depicted in FIG. 1. In other embodiments, the bounding box is manually constructed by an operator of the system. The bounding box may be used to delineate a starting point within the image for sampling.

One example method for tracking structures in the image of a patient is to use discrete structure forests. Discrete structure forests are a random forest classifier. A random forest includes a decision tree where each node in the tree corresponds to a decision that the system makes. In some embodiments, the features used as decision points in the tree follow geometric patterns that encode the underlying structure of the target being tracked. The use of discrete structure forests is a type of data mining or machine learning that allows a system to learn the structure of a target as the target is being tracked in the images of the patient. For example, features of the potential object moving in synchronization with the inserted catheter are sampled and feature point comparisons are performed to capture the underlying structure of the object in the images. The sampling techniques may be random sampling, data driven sampling, manually designed pattern sampling, or other sampling.

The discrete structure forest is constructed by first building directed random feature chains. The processor 14 may build the discrete structure forest, as well as the directed random feature chains, alone or in conjunction with the scanner 12 or memory 16. In one embodiment, sampling starts with a point $X_0$ inside the region of the image where the object (e.g., anatomy of interest) has been detected. In one embodiment, if a bounding box is being used, the point $X_0$ may be the center of the bounding box. An additional feature point $X_1$ is sampled within the neighborhood of $X_0$. The two points are used as a direction for continued sampling of points within the detected object. When sampling $X_n$, points $X_{n-1}$ and $X_{n-2}$ are used to avoid any cross over or overlaps in the direction for continued sampling. The direction may be a chain in the detected object represented as:

$X_{i-1} \to X_i \to X_{i+1} \to X_{i+2} \to \ldots X_n$. The next point in the chain may be sampled by satisfying the following constraints:

$$\max(X_{i-1}, X_{i-1} + \alpha(X_i - X_{i-1})) < X_{i+1} \quad \text{(Eq. 6)}$$

$$X_{i+1} < \min(X_{i-1} + \beta(X_i - X_{i-1}), B_{dim}) \quad \text{(Eq. 7)}$$

where $0 < \alpha < 1$ and $\beta > 1$. The processor 12 may perform the calculations for these equations alone or in conjunction with the memory 16.

Another approach may use data driven pairwise features. Data driven pairwise features try to encode gradient changes within the detected object, such as edges. The image is combined with a Gaussian kernel of a standard deviation of three, or other number of pixels, to suppress noise in the image. Other standard deviations of pixels may be used. Edge detection is then performed on a bounding box around the object. The number of points within the bounding box is approximated from 0 to K. The approximation limits the points to points within the neighborhood of the detected object. Points are sampled along the edge and the for each edge point $X_{max}$, a pair of points around $X_{max}$ are sampled such that the pair of points are collinear, equidistant and on the opposite sides of $X_{max}$. If $X_j$ and $X_k$ are two points sampled around $X_{max}$ then the following formula may be used:

$$\frac{|\langle X_{max} - X_j, X_{max} - X_k \rangle|}{\|X_{max} - X_j\|_2 \cdot \|X_{max} - X_k\|_2} \quad \text{(Eq. 8)}$$

This formula allows for the identification of edges of the object in the bounding box.

In another embodiment, data driven feature chains may be used. A data driven feature chain identifies and tracks the object by sampling maximum or minimum points within the object. An extremum point within the object is sampled and the next nearest extremum point is sampled. The sampled points form a chain. Additional points are sampled until a certain predefined length is reached for the chain of sampled points. The chain may be used as a known location at the time the image was taken and used as an input for tracking the location of the structure in future images of the patient. Data driven feature chains show significant robustness to intensity fluctuations in the image data because the fluctuations do not affect the order relationship between extrema.

Manually drawn feature trackers may be employed. Specific domain knowledge, for example typical density or shape of calcium deposits is known in advance, may be used to construct the manually drawn feature tracker, such as a geometric shape. The manually drawn feature tracker is then used in a similar fashion to a bounding box. The tracker is applied to the image, and then the location is used to project where the detected structure will be in subsequent images. In some embodiments, a triangular pyramid shape may be used to sample points inside the object corresponding to the position of the triangular pyramid. This approach may be used for dense calcium deposits that are not necessarily elongated tube like calcium deposits.

The above described sampling approaches, random sampling, data driven sampling, and manually designed pattern sampling may be implemented by the processor 12 alone or in conjunction with the memory 16. The sampling approaches may be used in conjunction with the object detection process of using an inserted catheter to detect objects via their movement in sync with the inserted catheter.

In act 32, a processor may output an image of the structure. The image may be output to a display that is a part of the system depicted in FIG. 1. The outputted image may be of the structure as the structure moves in concert with the catheter or anatomical structure to which the catheter is affixed. In other embodiments the processor may output a static image of the structure. In yet other embodiments, the image is output continuously during an operation on the patient. The images may be output to a display that is included in the system depicted in FIG. 1.

Using the detection and tracking, the anatomical structure of interest may be highlighted. In one embodiment, the anatomical structure is segmented. The segmented structure being shown alone highlights the anatomy of interest. In other embodiments, color, graphics, or intensity change are used to highlight the anatomical structure relative to other anatomy or background in the image.

FIG. 3 shows a sample flowchart for detect and tracking an inserted catheter, such as a pigtail catheter, using the system of FIG. 1, and the embodiments disclosed herein. A pigtail catheter is inserted into a patient. The pigtail catheter is detected. The detection may use offline trained detectors for pigtail catheter detection. The pigtail catheter is tracked and automatic discovery of supporting structures occurs. The discovered supporting structures may be used to predict the position of an aortic root. The catheter motion is used to identify the aortic root as the anatomical structure of interest. If necessary, the pigtail catheter may be removed.

FIG. 4 is an alternative workflow that includes detecting objects in a context region in the image data of a patient. A catheter is inserted into a patient by a surgeon. The catheter is detected and tracked. The workflow may use offline trained pigtail catheter detection. A context region that relates to the pigtail catheter may be discovered. The relationship is similar motion. The context region is tracked rather than specific anatomy. Additional regions may be discovered and tracked. The catheter may be withdrawn by the surgeon if necessary. The workflow in FIG. 4 is iterative and may be repeated throughout the duration of a procedure.

Figure 5:
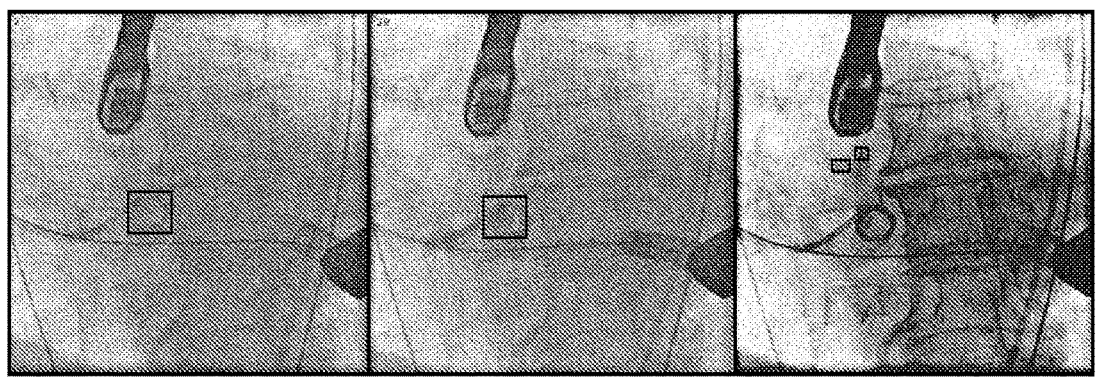
FIG. 5 shows example fluoroscopic images of an inserted pigtail catheter in a patient.

FIG. 5 shows an example of the detecting and tracking disclosed herein. At 50, the result of a pigtail catheter that has been detected and tracked according to the method disclosed herein is shown. At 52, calcium deposits and the detected pigtail catheter are shown. The calcium deposits are detected as moving in concert with the inserted catheter. At 54, the calcium deposits above the detected pigtail catheter have been detected according to the methods disclosed herein and will be tracked.

Figure 6:
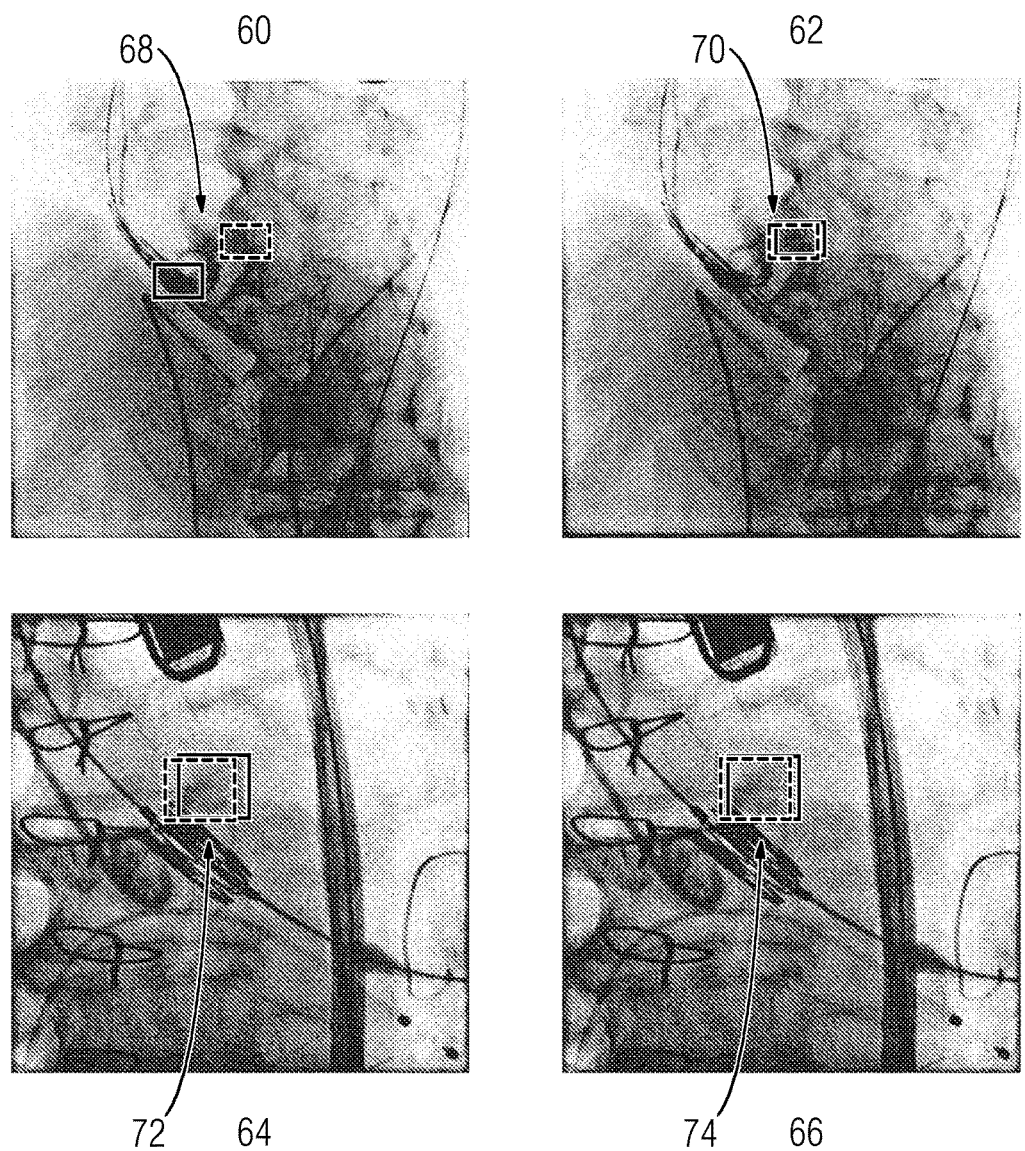
FIG. 6 shows an example comparison between existing methods for tracking anatomical structures versus the approach detailed in this application for tracking anatomical structures.

FIG. 6 shows an example comparison of existing tracking methods for object detection versus the proposed tracking method for object detection in this disclosure. The two images 60 and 64 show the use of a tracking learning detection approach to object detection and tracking. The tracking learning detection approach includes using an initial template to track an object and then collects additional samples of the object in subsequent images to update the object location in subsequent images. The two images 62 and 66 show object detection and tracking using discrete structure forests and random forests. The two boxes shown in 60 at 68 and the two boxes shown in 62 at 70 correspond to the actual location (lighter box) of calcium deposit and the tracking result (darker box) for the two different approaches. In image 62 at box 70, it is clear that the actual location and the tracking result of the discrete structure forest approach are very close. In image 60, at box 68, there is a large difference between the actual location and the tracking result of the tracking learning detection method. Similarly, the two boxes shown in 64 at 72 and the two boxes in 66 shown at 74 show the difference between the two approaches. At 72, there is a noticeable difference between the actual location and the result of the tracking learning detection method. At 74, there is less difference between the discrete structure forest approach results and the actual location.

FIG. 1 shows a system for tracking structures in images of a patient. The system includes a scanner 12, a memory 16, and a processor 14. In some embodiments, a display is attached to the system. Additional, different, or fewer components may be provided. For example, a network or network connection is provided, such as for networking from the scanner 12 to a remote computer or server. In another example, a user interface is provided. As another example, scanner 12 is not provided. Instead, a computer or server detects and tracks the structures from received image data of the patient.

The processor 14, memory 16, and scanner 12 are part of the system. Alternatively, the processor 14, memory 16, and scanner 12 are part of a server, computer, and/or image processing system separate from the system depicted in FIG. 1. In other embodiments, the processor 14, memory 16, and a display are a personal computer, such as desktop or laptop, a workstation, a server, a network, or combinations thereof. The processor 14, display, and memory 16 may be provided without other components for detecting and tracking objects in image data of the patient.

The scanner 12 may be a fluoroscopic image scanner. The fluoroscopic image scanner transmits x-rays through a patient. The x-rays are detected as intensities that vary based on the density of tissue or structure in the patient through which the x-rays pass. The scanner may also be used in conjunction with a contrast agent to help illuminate and identify human organs. The resulting fluoroscopic image portrays the anatomical structure that is detected and tracked.

The memory 16 may be a graphics processing memory, a video random access memory, a random access memory, system memory, cache memory, hard drive, optical media, magnetic media, flash drive, buffer, database, combinations thereof, or other now known or later developed memory device for storing data. The memory 16 is part of the system depicted in FIG. 1, part of a computer associated with the processor 14, part of a database, part of another system, or a standalone device.

The memory 16 stores image data, such as fluoroscopic image data of a patient. The fluoroscopic image data represents a projection through a volume of the patient. The memory 16 may alternatively or additionally store data during processing, such as storing filtered data, possible object locations, extracted feature values, actual object locations, cluster labels, imaging data, and/or other information discussed herein.

The memory 16 or other memory is alternatively or additionally a non-transitory computer readable storage medium storing data representing instructions executable by the programmed processor 14 for tracking anatomical structures in images of a patient. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 14 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for detecting and tracking a catheter and anatomic or other structure. The processor 14 is a single device or multiple devices operating in serial, parallel, or separately. The processor 14 may be a main processor of a computer, such as a laptop or desktop computer, or may be a processor for handling some tasks in a larger system, such as in an imaging system. The processor 14 is configured by instructions, design, hardware, and/or software to perform the acts discussed herein. The processor 14 is configured to perform the acts discussed above. The processor 14 may be configured to generate a user interface for receiving corrections or verification of the detecting and tracking of objects.

The system depicted in FIG. 1 may also include a display. The display may be a monitor, LCD, projector, plasma display, CRT, printer, or other now known or later developed devise for outputting visual information. The display receives images, graphics, text, quantities, or other information from the processor 14, memory 16, or scanner 12. One or more images are displayed. The images are of the detected object in the patient, the inserted catheter, as well as the movement of the anatomy of the patient. The images may be streamed during a procedure, or the images may be still images.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for structure detection, the method comprising:
   scanning, over time, an object having an inserted catheter;
   detecting, by a processor, the catheter as represented in data from the scanning;
   tracking, by the processor, a movement of the catheter represented in the data from the scanning using a known shape or first structure of the catheter;
   detecting, by the processor, a second structure represented in the data from the scanning based on the movement of the catheter, the second structure detected as moving in synchronization with the catheter;
   tracking, by the processor, the second structure represented in the data from the scanning, the tracking using sampling of less than all of the second structure, the sampling being a plurality of the features of the second structure, and the sampling applied to locations represented in the data, the locations based on a previous location of the second structure; and outputting, by the processor, an image of the second structure.

2. The method of claim 1, wherein the catheter is a pigtail catheter.

3. The method of claim 1, wherein the catheter is located at the aortic root of the object.

4. The method of claim 1, wherein the data from the scanning includes a plurality of fluoroscopic images.

5. The method of claim 1, further comprising:
removing the inserted catheter.

6. The method of claim 1, further comprising:
constructing a bounding box around the detected second structure; and
wherein tracking the structure includes sampling within the limits defined by the bounding box.

7. The method of claim 1, wherein the tracking of the second structure includes using a discrete structure forest to track features of the second structure.

8. The method of claim 7, wherein tracking the second structure comprises tracking the density of the second structure, tracking the contrast between the second structure and surrounding areas in the data, random sampling of points in the second structure and outside the second structure, or a combination thereof.

9. The method of claim 1, wherein the second structure is an inserted object separate from the catheter.

10. A system for object detection over time in a first structure having an inserted catheter, the system comprising:
a scanner configured to image the structure containing the inserted catheter over time;
a processor configured to detect and track the catheter as represented in data from the imaging using a known shape or second structure of the catheter;
the processor configured to further detect and track an object represented in the data from the imaging based on the catheter, the object detected based on its linear motion correlation with the inserted catheter, wherein the object is tracked using sampling applied to locations represented in the data, the locations based on a previous location of the object; and
the processor configured to output an image of the object.

11. The system of claim 10, wherein the catheter is a pigtail catheter.

12. The system of claim 10, wherein the data from the image includes a plurality of fluoroscopic images.

13. The system of claim 10, wherein the processor is configured to construct a bounding box around the detected object; and wherein the sampling includes sampling within the bounding box.

14. The system of claim 10, wherein the processor is configured to track the object including using a discrete structure forest to track features of the object.

15. The system of claim 14, wherein the processor is configured to track the object by a density of the object, a contrast between the object and surrounding areas in the data, a random sampling of points in the data, or a combination thereof.

16. A non-transitory computer readable storage medium having stored therein data representing instructions executable by a programmed processor for facilitating detection of an object in a patient, the storage medium comprising instructions for:
scanning over time a patient having an inserted pig tail catheter;
detecting the pig tail catheter as represented in data from the scanning;
tracking a movement of the pig tail catheter in the data from the scanning using a known shape or first structure of the pig tail catheter;
detecting a second structure represented in the data from the scanning based on the movement of the pigtail catheter, the second structure detected based on its linear motion correlation moving in synchronization with the inserted catheter;
tracking the second structure represented in the data from the scanning, the tracking using sampling of less than all of the second structure as a plurality of the features of the second structure, the sampling applied to locations represented in the data, the locations based on a previous location of the second structure; and
outputting an image of the second structure.

17. The non-transitory computer readable storage medium of claim 16 wherein the data from the scanning includes a plurality of fluoroscopic images.

18. The non-transitory computer readable storage medium of claim 16, further comprising constructing a bounding box around the detected second structure; and wherein tracking the second structure includes sampling within the limits defined by the bounding box.

19. The non-transitory computer readable storage medium of claim 16, wherein tracking the second structure includes using a discrete structure forest to track features of the second structure.

20. The non-transitory computer readable storage medium of claim 19, wherein tracking the second structure includes tracking a density of the second structure, tracking a contrast between the second structure and surrounding areas in the data, a random sampling of points in the data, or a combination thereof.

* * * * *